(12) United States Patent
Nagasaka

(10) Patent No.: US 11,852,515 B2
(45) Date of Patent: Dec. 26, 2023

(54) FLUID MEASUREMENT APPARATUS, FLUID MEASUREMENT METHOD, AND PROGRAM

(71) Applicant: KYOCERA Corporation, Kyoto (JP)

(72) Inventor: Yushi Nagasaka, Otsu (JP)

(73) Assignee: KYOCERA CORPORATION, Kyoto (JP)

( * ) Notice: Subject to any disclaimer, the term of this patent is extended or adjusted under 35 U.S.C. 154(b) by 592 days.

(21) Appl. No.: 16/964,907

(22) PCT Filed: Jan. 25, 2019

(86) PCT No.: PCT/JP2019/002515
§ 371 (c)(1),
(2) Date: Jul. 24, 2020

(87) PCT Pub. No.: WO2019/146762
PCT Pub. Date: Aug. 1, 2019

(65) Prior Publication Data
US 2021/0033438 A1  Feb. 4, 2021

(30) Foreign Application Priority Data

Jan. 26, 2018  (JP) ................. 2018-011816

(51) Int. Cl.
*G01F 1/661* (2022.01)
*A61B 5/026* (2006.01)
*A61B 5/0285* (2006.01)

(52) U.S. Cl.
CPC ............ *G01F 1/661* (2013.01); *A61B 5/0261* (2013.01); *A61B 5/0285* (2013.01)

(58) Field of Classification Search
CPC ...... G01F 1/661; A61B 5/0261; A61B 5/0285
See application file for complete search history.

(56) References Cited

U.S. PATENT DOCUMENTS

| 3,552,855 A | * | 1/1971 | Crosswy et al. ....... H01S 3/083 356/28 |
| 3,675,029 A | * | 7/1972 | Iten ......................... G01F 1/661 356/28 |
| 3,765,768 A | * | 10/1973 | Budin ..................... G01S 17/14 356/28 |

(Continued)

FOREIGN PATENT DOCUMENTS

| EP | 3045876 A1 | 7/2016 |
| JP | 2006-126114 A | 5/2006 |

(Continued)

OTHER PUBLICATIONS

Translation of WO-2015033469-A1 (Year: 2015).*
Translation of Clot et al. WO-9533998-A1 (Year: 1995).*

*Primary Examiner* — Nathaniel T Woodward
(74) *Attorney, Agent, or Firm* — Procopio, Cory, Hargreaves & Savitch LLP

(57) ABSTRACT

A fluid measurement apparatus comprises: a first optical emitter configured to emit light to an irradiated object that includes a fluid; an optical detector configured to receive first received light emitted from the first optical emitter and transmitted through the fluid to thereby be shifted in frequency; and an estimation unit configured to estimate a flow state of the fluid based on the first received light.

14 Claims, 10 Drawing Sheets

(56) References Cited

U.S. PATENT DOCUMENTS

2011/0285984 A1* 11/2011 Christian .............. G01S 7/4812
356/28.5
2019/0380598 A1 12/2019 Higuchi

FOREIGN PATENT DOCUMENTS

| | | | |
|---|---|---|---|
| JP | 2017-113320 A | 6/2017 | |
| JP | 2018-7894 A | 1/2018 | |
| WO | WO-9533998 A1 * | 12/1995 | .............. G01P 3/366 |
| WO | 2015/033469 A1 | 3/2015 | |
| WO | WO-2015033469 A1 * | 3/2015 | .............. G01F 1/661 |
| WO | 2016/092679 A1 | 6/2016 | |
| WO | 2016/132512 A1 | 8/2016 | |

* cited by examiner

FLUID MEASUREMENT APPARATUS, FLUID MEASUREMENT METHOD, AND PROGRAM

CROSS REFERENCE TO RELATED APPLICATION

This application claims priority to and the benefit of Japanese Patent Application No. 2018-11816 filed on Jan. 26, 2018, the entire disclosure of which is incorporated herein by reference.

TECHNICAL FIELD

The present disclosure relates to a fluid measurement apparatus, a fluid measurement method, and a program.

BACKGROUND

Fluid measurement apparatuses for measuring the velocity, flow amount, etc. of a fluid flowing in a flow channel are studied in recent years. For example, JP 2017-113320 A (PTL 1) discloses a fluid evaluation apparatus that obtains at least one of the flow amount and flow velocity of a fluid flowing inside a tube, a living body, or the like.

CITATION LIST

Patent Literature

PTL 1: JP 2017-113320 A

SUMMARY

A measurement apparatus according to an embodiment comprises: a first optical emitter configured to emit light to an irradiated object that includes a fluid; an optical detector configured to receive first received light emitted from the first optical emitter and transmitted through the fluid to thereby be shifted in frequency; and an estimation unit configured to estimate a flow state of the fluid based on the first received light.

A fluid measurement method according to an embodiment comprises: emitting light to an irradiated object that includes a fluid; receiving first received light transmitted through the fluid to thereby be shifted in frequency; and estimating a flow state of the fluid based on the first received light.

A program according to an embodiment causes a computer to execute: emitting light from a first optical emitter to an irradiated object that includes a fluid; receiving, by an optical detector, first received light emitted from the first optical emitter and transmitted through the fluid to thereby be shifted in frequency; and estimating, by an estimation unit, a flow state of the fluid based on the first received light.

BRIEF DESCRIPTION OF THE DRAWINGS

In the accompanying drawings.

DETAILED DESCRIPTION

A fluid measurement apparatus can be more convenient if it is capable of estimating a flow state of a fluid under various conditions. The present disclosure relates to providing a highly convenient fluid measurement apparatus, fluid measurement method, and program. According to an embodiment, it is possible to provide a highly convenient fluid measurement apparatus, fluid measurement method, and program. An embodiment of the present disclosure will be described below, with reference to the drawings. First, a structure of a fluid measurement apparatus according to an embodiment will be described below.

Figure 1:
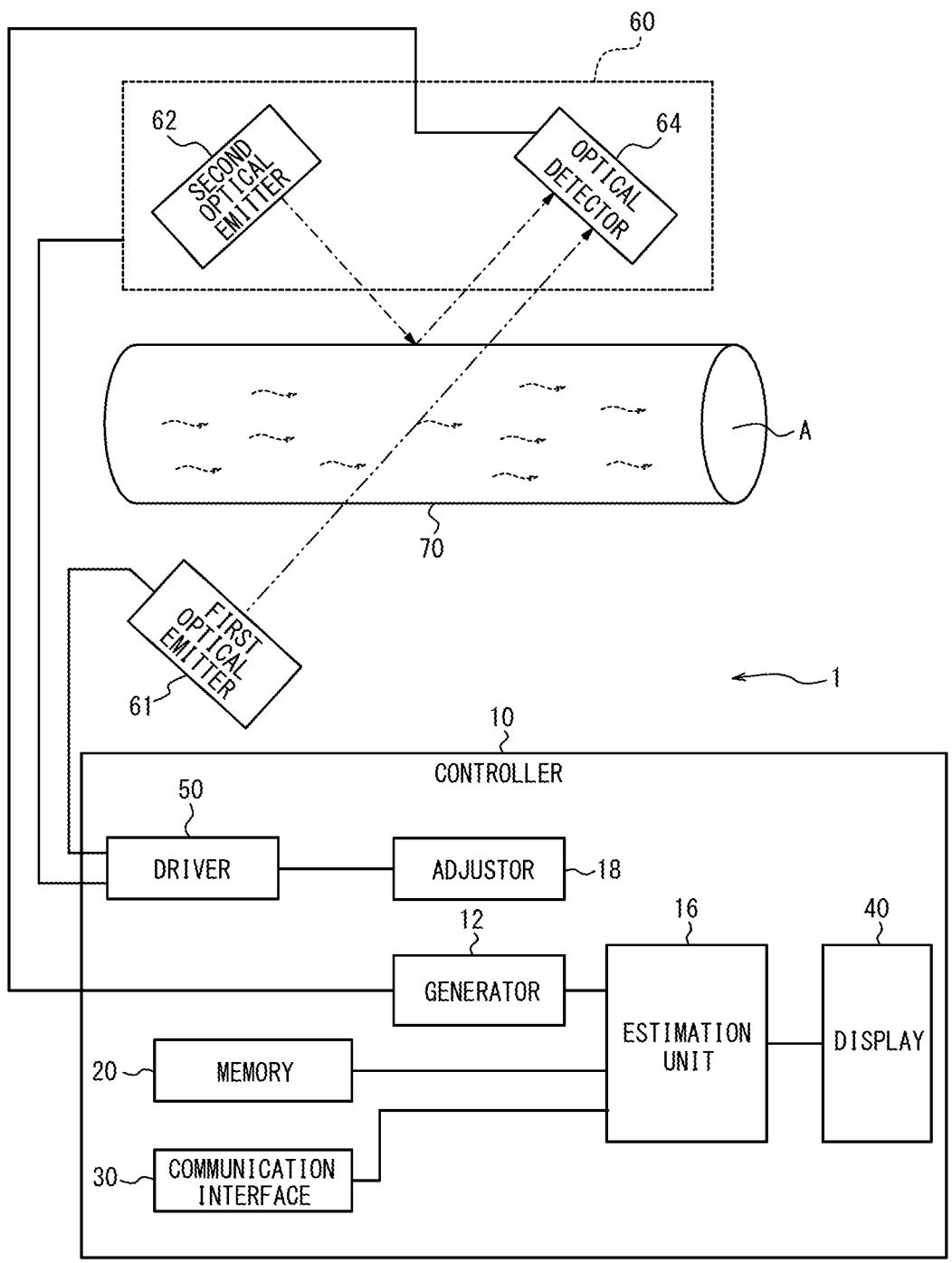
FIG. 1 is a block diagram illustrating an example of a schematic structure of a fluid measurement apparatus according to an embodiment.

FIG. 1 is a block diagram illustrating an example of a schematic structure of a fluid measurement apparatus according to an embodiment. A power source that supplies power to each functional unit, a structure of supplying power from the power source to each functional unit, and the like are not illustrated in the drawing. Functional units illustrated in FIG. 1 may be included in or omitted from a fluid measurement apparatus 1 according to an embodiment as appropriate.

The fluid measurement apparatus according to an embodiment can measure a flow state (e.g. flow velocity or flow amount) of a flowing object (fluid). Specifically, the fluid measurement apparatus can calculate the flow amount or flow velocity of the fluid as the flow state of the fluid. The flow amount is the volume or mass of the fluid flowing per unit time, and the flow velocity is the distance the fluid travels per unit time.

The fluid measurement apparatus can calculate the flow state of the fluid using the Doppler effect of light. Light applied to an irradiated object (the fluid, a flow channel in which the fluid flows, and the like) is scattered by the fluid, and its frequency is shifted (Doppler-shifted) due to the Doppler effect depending on the flow state of the fluid. Hence, the Doppler effect can be used to calculate the flow state. Specifically, the fluid measurement apparatus can emit light from an optical emitter toward the irradiated object including the fluid to be measured, and receive, by an optical detector, interference light including light scattered by the irradiated object. The fluid measurement apparatus can then calculate the flow state of the fluid based on the output of the optical detector.

The fluid to be measured is not limited, as long as it has translucency and its flow state can be calculated using the Doppler effect of light. Specifically, the fluid is any fluid that scatters light by itself or contains a substance (scattering substance) that scatters light. Examples of the fluid include liquids such as water, blood, milk, printer ink, and oil, and gases containing solids such as a powder. At least part of the fluid has translucency. In the case where the flow of the scattering substance, the powder, or the like follows the flow of the fluid, the fluid measurement apparatus may regard the flow amount or flow velocity of the scattering substance, the powder, or the like as the flow amount or velocity of the fluid. That is, the "flow amount or flow velocity of the fluid" can be interpreted as the "flow amount or flow velocity of the scattering substance, the powder, or the like".

The fluid measurement apparatus 1 according to an embodiment includes an estimation unit 16 that estimates the flow state based on received light. The fluid measurement apparatus 1 according to an embodiment may also include, for example, at least one of a sensor 60 and a first optical emitter 61. In the fluid measurement apparatus according to an embodiment, the first optical emitter 61 can emit light such as laser light toward a flow channel 70. The sensor 60 can perform detection relating to a fluid A flowing in the flow channel 70. The estimation unit 16 can estimate the flow state of the fluid A flowing in the flow channel 70, based on the result of detection by the sensor 60.

The first optical emitter 61 is positioned with respect to the flow channel 70 so that light can be emitted toward the fluid A flowing in the flow channel 70. The sensor 60 is positioned with respect to the flow channel 70 so that the flow state of the fluid A flowing in the flow channel 70 can be estimated. The sensor 60 includes a second optical emitter 62 and an optical detector 64.

In the fluid measurement apparatus according to an embodiment, the first optical emitter 61, the second optical emitter 62, the optical detector 64, and the flow channel 70 are positioned as appropriate so as to satisfy the following conditions:

(1) At least part of light emitted from the first optical emitter 61 is transmitted through the flow channel 70 (i.e. the fluid A flowing in the flow channel 70) and then received by the optical detector 64.

(2) At least part of light emitted from the second optical emitter 62 is reflected by the flow channel 70 and then received by the optical detector 64.

The first optical emitter 61 and the second optical emitter 62 may each be composed of, for example, any number of laser diodes (LDs). The first optical emitter 61 and the second optical emitter 62 can emit light toward the flow channel 70. Specifically, the first optical emitter 61 and the second optical emitter 62 can emit laser light or the like. The first optical emitter 61 and the second optical emitter 62 may each be any optical emitter capable of emitting light of a wavelength with which the measured object contained in the fluid A is detectable.

A driver 50 can drive the first optical emitter 61, the second optical emitter 62, and the optical detector 64. The driver 50 may be composed of, for example, any laser drive circuit. The driver 50 may be included in the fluid measurement apparatus 1, or provided outside the fluid measurement apparatus 1. The driver 50 may be included in the sensor 60, or provided outside the sensor 60.

The optical detector 64 may be composed of, for example, any number of photodiodes (PDs). The optical detector 64 can receive at least part of at least one of light emitted from the first optical emitter 61 and light emitted from the second optical emitter 62. The optical detector 64 can receive light (transmitted light) transmitted through the fluid A in the flow channel 70 from among the light emitted from the first optical emitter 61 toward the flow channel 70. That is, the optical detector 64 can receive light (forward scattered light) scattered forward by the fluid A. The optical detector 64 can also receive light (reflected light) reflected by the flow channel 70 from among the light emitted from the second optical emitter 62 toward the flow channel 70.

A signal relating to the intensity of light (received light) received by the optical detector 64 is transmitted to a generator 12. The generator 12 will be described later. The fluid measurement apparatus 1 may use any type of amplifier and/or filter (not illustrated) when transmitting the signal relating to the intensity of the received light to the generator 12 and processing it.

The flow channel 70 in which the fluid A flows may be a tubular member made of any type of material. The flow channel 70 may be configured to prevent the fluid A from leaking so that the flow state of the fluid A can be measured appropriately. For example, the flow channel 70 may be a tube made of plastic, vinyl chloride, glass, or the like. The flow channel 70 may be a tissue forming a flow channel through which a body fluid of a human, an animal, or the like flows, such as a blood vessel. The flow channel 70 may be made of a material that transmits at least part of light emitted from the first optical emitter 61 and/or light emitted from the second optical emitter 62. The shape of the flow channel 70 is not limited, as long as it allows the fluid A to flow. The shape of the flow channel 70 may be, for example, any of a circle, a rectangle, and other polygons.

FIG. 1 schematically illustrates a state in which the fluid A flows in the flow channel 70. In the case where the fluid A contains particles or fine particles, the particles or fine particles contained in the fluid A move with the flow of the fluid A.

The first optical emitter 61 is positioned with respect to the flow channel 70 and/or the sensor 60 so that the flow state of the fluid A flowing in the flow channel 70 can be appropriately measured by the sensor 60. Specifically, the first optical emitter 61 is positioned so that light can be appropriately emitted to the fluid A flowing in the flow channel 70. The first optical emitter 61 is also positioned with respect to the flow channel 70 and/or the optical detector 64 so that light emitted from the first optical emitter 61 and transmitted through the flow channel 70 and the fluid A can be appropriately received by the optical detector 64. In an embodiment, the first optical emitter 61 and the second optical emitter 62 may be arranged on opposite sides of the flow channel 70, in a planar view in a direction in which the fluid A flows in the flow channel 70. That is, the first optical emitter 61 and the second optical emitter 62 may be arranged on opposite sides with the flow channel 70 therebetween. This allows the optical detector 64 to receive both transmitted light and reflected light.

In the sensor 60, the second optical emitter 62 and/or the optical detector 64 are positioned with respect to the flow channel 70 so that the flow state of the fluid A flowing in the flow channel 70 can be measured appropriately. Specifically, the second optical emitter 62 is positioned so that light can be appropriately emitted to the flow channel 70. The optical detector 64 is positioned so that light emitted from the second optical emitter 62 and reflected by the flow channel 70 can be received appropriately.

Instead of the sensor 60 including the second optical emitter 62 and the optical detector 64 in one package, the second optical emitter 62 and the optical detector 64 may be provided separately. The first optical emitter 61 may be a part of a sensor of one package including the optical detector.

The fluid measurement apparatus 1 will be described in more detail below.

The fluid measurement apparatus 1 includes a controller 10 that controls the whole apparatus. The controller 10 includes the generator 12 and the estimation unit 16. The controller 10 may also include an adjustor 18. The controller 10 may also include at least one of a memory 20, a communication interface 30, a display 40, and the driver 50 as appropriate.

The controller 10 includes at least one processor such as a central processing unit (CPU), to provide control and processing capacity for achieving various functions of the generator 12, the estimation unit 16, the adjustor 18, and the like. The controller 10 may implement the functions of the generator 12, the estimation unit 16, the adjustor 18, and the like by one processor, by several processors, or by respective separate processors. Each processor may be implemented as a single integrated circuit. Each processor may be implemented as a plurality of integrated circuits and/or discrete circuits communicably connected to one another. Each processor may be implemented based on any of various conventionally known techniques. In an embodiment, the functions of the generator 12, the estimation unit 16, and the adjustor 18 may be implemented, for example, by a CPU and a program executed by the CPU.

The generator 12 generates a frequency spectrum S according to an embodiment. The generation of the frequency spectrum S by the generator 12 will be described in detail later. The estimation unit 16 can estimate the flow state of the fluid A based on the frequency spectrum S. The estimation of the flow state of the fluid A by the estimation unit 16 will be described in detail later. The adjustor 18 can adjust the light quantity of light received by the optical detector 64, by adjusting, for example, the intensity of light emitted from the first optical emitter 61 and received by the optical detector 64 and/or the intensity of light emitted from the second optical emitter 62 and received by the optical detector 64. The adjustment of the light quantity by the adjustor 18 will be described in detail later. The "light quantity" herein refers to the quantity of light received by the optical detector 64, and indicates the amount of light energy.

The memory 20 may include semiconductor memory, magnetic memory, etc. The memory 20 may store various information, programs to be executed, and the like. The memory 20 may function, for example, as working memory of the generator 12 and/or the estimation unit 16. In an embodiment, the memory 20 may store various information used to estimate the flow state of the fluid A from the frequency spectrum S generated by the generator 12. The memory 20 may store the foregoing various information beforehand, or acquire the information through external communication or the like and store them. The memory 20 may store the foregoing various information as any of various memory cards. The memory 20 may be included in, for example, the generator 12 and/or the estimation unit 16.

The communication interface 30 can achieve various functions such as wireless communication. The communication interface 30 may achieve communication by any of various communication systems such as Long Term Evolution (LTE). The communication interface 30 may include a modem with a communication system standardized in the International Telecommunication Union Telecommunication Standardization Sector (ITU-T), for example. The communication interface 30 may, for example, wirelessly communicate with an external apparatus such as an external server or a cloud server via a network, through an antenna. In an embodiment, the communication interface 30 may receive the foregoing various information from an external database such as an external server or a cloud server. Such information received by the communication interface 30 may be stored in the memory 20.

The display 40 can provide information such as the flow state of the fluid A to a user as video, by displaying the measurement result of the flow state of the fluid A or the like on a display device such as a liquid crystal display (LCD), an organic EL display, or an inorganic EL display. The display 40 may display images of characters, figures, signs, graphs, and the like on the display device. The display 40 may display images of objects for operation and the like on the display device.

The form of information presented by the display 40 is not limited to a form that has visual effect on the user. For example, the display 40 may output information such as the flow state of the fluid A from an audio device such as a speaker as sound. The display 40 may provide information such as the measurement result to the user as sound and video, using the audio device and the display device. The display 40 may have any structure that can notify the user of the flow state of the fluid A.

The memory 20, the communication interface 30, the display 40, and the driver 50 may each be included in the fluid measurement apparatus 1 or provided outside the fluid measurement apparatus 1. For example, the display device may be included in the sensor 60 or provided outside the sensor 60.

Detection of scattered light in fluid measurement according to an embodiment will be described below.

Figure 2:
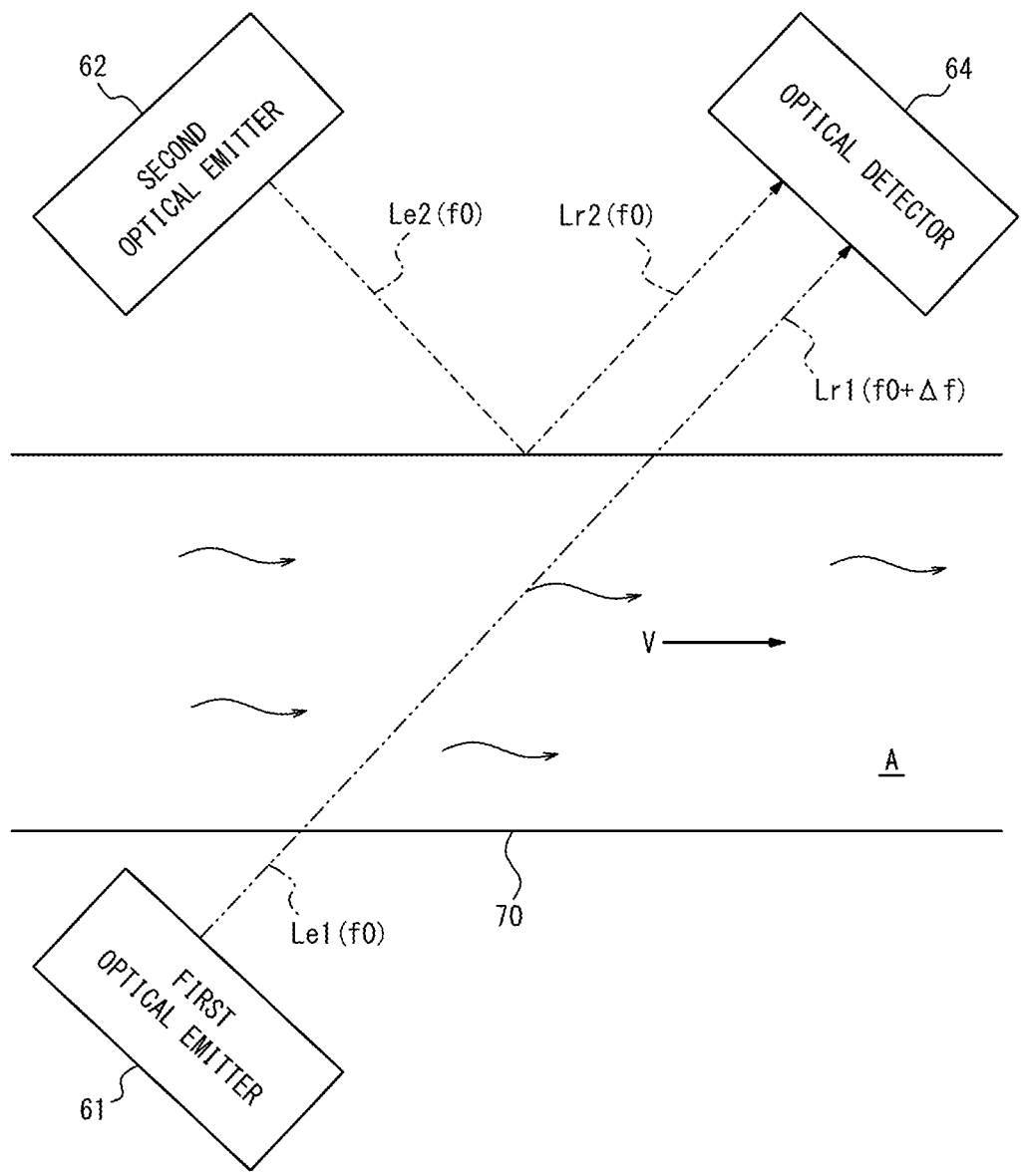
FIG. 2 is a diagram for explaining detection of scattered light in fluid measurement according to an embodiment.

FIG. 2 is a diagram for explaining detection of scattered light in fluid measurement according to an embodiment. The first optical emitter 61, the second optical emitter 62 and the optical detector 64 in the sensor 60, and the flow channel 70 in which the fluid A flows are enlarged in the drawing. FIG. 2 schematically illustrates a state in which the fluid A flows in the right direction at a velocity V in the flow channel 70. In the case where the fluid A contains fine particles, the fine particles flow at the velocity V in the flow channel 70, too.

Light emitted from the first optical emitter 61 toward the flow channel 70 includes incident light Le1. The incident light Le1 is light of a frequency f0 when emitted from the first optical emitter 61. The incident light Le1 of the frequency f0 is denoted by Le1(f0).

Light emitted from the second optical emitter 62 toward the flow channel 70 includes incident light Le2. The incident light Le2 is light of the frequency f0 when emitted from the second optical emitter 62. The incident light Le2 of the frequency f0 is denoted by Le2(f0).

The incident light Le2 is reflected by the flow channel 70. That is, the incident light Le2 is not scattered by the fluid A but scattered by the flow channel 70 to become scattered light Lr2. The scattered light Lr2 results from scattering of the incident light Le2 by the stationary flow channel 70. Here, the frequency f0 of the incident light Le2 is unchanged. The scattered light Lr2 of the frequency f0 is denoted by Lr2(f0). Hereafter, light not shifted in frequency from among light emitted from the second optical emitter 62 and received by the optical detector 64 is also referred to as "second light Lr2".

At least part of the incident light Le1 is not reflected by the flow channel 70 but transmitted through the flow channel 70. That is, at least part of the incident light Le1 is not scattered by the flow channel 70 but scattered by the fluid A to become scattered light Lr1. Here, the frequency of the scattered light Lr1 is Doppler-shifted depending on the moving velocity of the fluid A, and as a result slightly changes from f0. The scattered light Lr1 whose frequency has changed from f0 by $\Delta f$ is denoted by Lr1(f0+$\Delta f$). Hereafter, light shifted in frequency as a result of being transmitted through the fluid A flowing in the flow channel 70 from among light emitted from the first optical emitter 61 and received by the optical detector 64 is also referred to as "first light Lr1".

The fluid measurement apparatus 1 according to an embodiment can estimate the flow state of the fluid A, based on output from the optical detector 64 that has received the scattered light Lr1 and the scattered light Lr2.

Fluid measurement by the fluid measurement apparatus 1 according to an embodiment will be described below.

Figure 3:
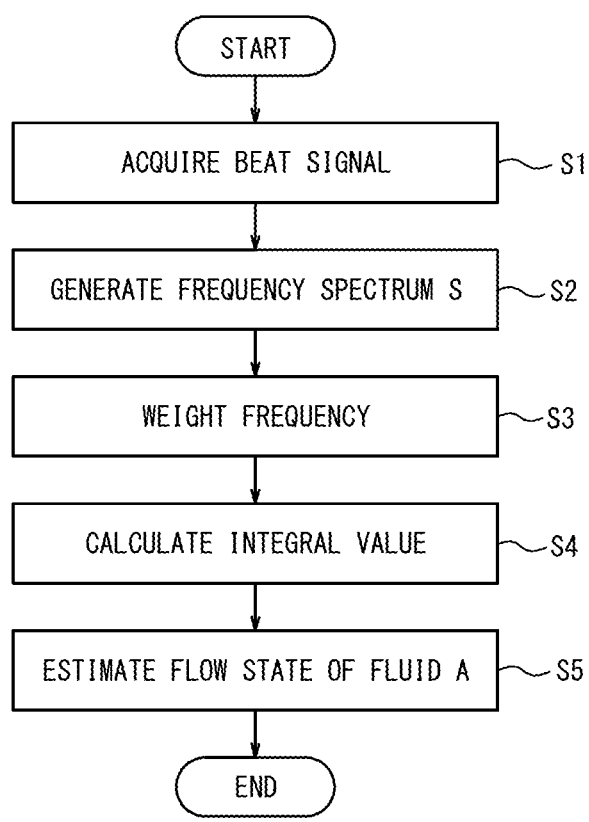
FIG. 3 is a flowchart illustrating fluid measurement according to an embodiment.

FIG. 3 is a flowchart illustrating fluid measurement according to an embodiment.

First, the generator 12 acquires a beat signal of interference light produced as a result of interference between scattered light (second light) Lr2 from the stationary flow channel 70 and scattered light (first light) Lr1 from the moving fluid A, based on output from the optical detector 64 (step S1). The beat signal indicates the relationship between the intensity of signal output from the optical detector 64 and time.

Figure 4:
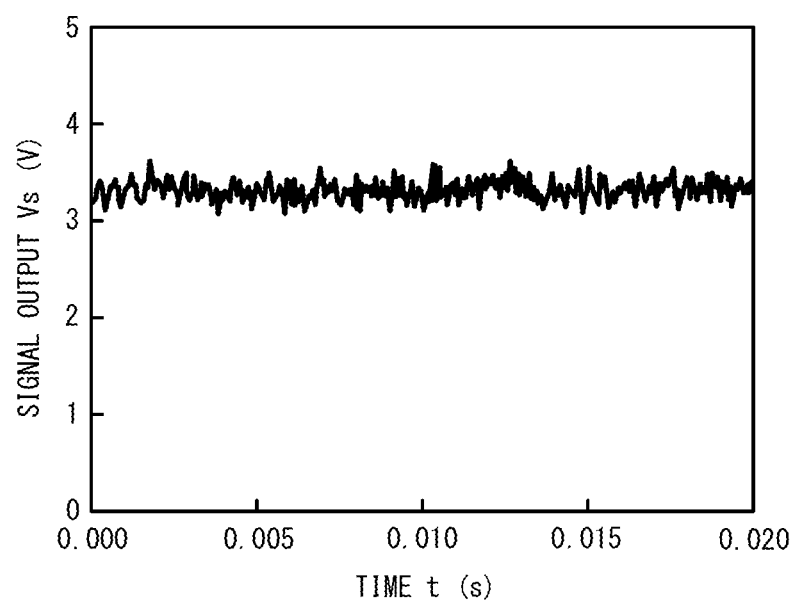
FIG. 4 is a diagram for explaining the principle of fluid measurement according to an embodiment.

FIG. 4 is a diagram illustrating an example of the beat signal acquired in step S1 in FIG. 3. In FIG. 4, the vertical axis represents the intensity of signal output, and the horizontal axis represents time. In the example illustrated in FIG. 4, the signal output from the optical detector 64 is voltage value, and is expressed in voltage unit (V) as signal output Vs. The beat signal is not limited to voltage, as long as it indicates temporal changes in the intensity of signal output. For example, the beat signal may be current value or resistance value.

After the beat signal is acquired in step S1, the generator 12 generates a frequency spectrum S from the acquired beat signal (step S2). The frequency spectrum S is a spectrum indicating signal intensity for each frequency component, and is generated based on the beat signal at a predetermined time. For example, in step S2, the generator 12 can generate the frequency spectrum S at the predetermined time by performing a fast Fourier transform (FFT) on the beat signal at the predetermined time acquired in step S1.

Figure 5:
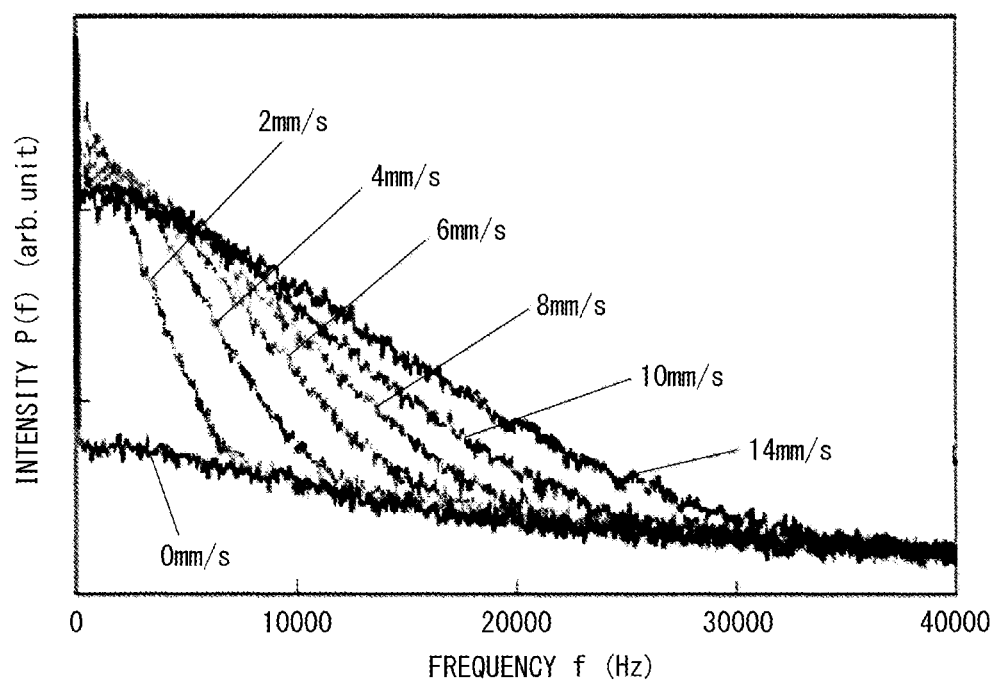
FIG. 5 is a diagram for explaining the principle of fluid measurement according to an embodiment.

FIG. 5 is a diagram illustrating an example of the frequency spectrum S generated in step S2 in FIG. 3. The frequency spectrum S represents the relationship between the intensity of signal output of the optical detector 64 at a predetermined time and frequency. In FIG. 5, the vertical axis represents intensity P(f) of signal output in arbitrary units, and the horizontal axis represents frequency f. Thus, the frequency spectrum S is a spectrum (frequency spectrum) representing power at the predetermined time as a function of frequency based on the beat signal. In this frequency spectrum of the beat signal, the Doppler shift frequency depends on the velocity of the fluid A.

FIG. 5 illustrates respective frequency spectra S generated from several beat signals acquired by changing the flow velocity of the fluid A. In FIG. 5, respective frequency spectra S in the cases where the flow velocity of the fluid A is 2 mm/s, 4 mm/s, 6 mm/s, 8 mm/s, 10 mm/s, and 14 mm/s are illustrated together, as an example. In an embodiment, respective frequency spectra S at a predetermined time can be generated. That is, each of the plurality of frequency spectra S illustrated in FIG. 5 is an instantaneous frequency spectrum at a predetermined time. In the frequency spectra S, the intensity on the high frequency side is higher when the flow velocity of the fluid A is faster. Thus, the frequency spectrum S depends on the flow state. Accordingly, the fluid measurement apparatus 1 can measure the flow state based on the frequency spectrum S. The frequency spectrum generated by performing an FFT on the beat signal as mentioned above is hereafter also referred to as "frequency spectrum P(f)".

After the frequency spectrum S is generated in step S2, the estimation unit 16 performs frequency weighting on the generated frequency spectrum P(f) according to the following Formula (1) (step S3):

$$f \cdot P(f) \quad (1)$$

After the frequency weighting is performed in step S3, the estimation unit 16 integrates the Formula (1) in an adequate frequency range to calculate an integral value expressed by the following Formula (2) (step S4):

$$\int f \cdot P(f) df \quad (2).$$

After the integral value is calculated in step S4, the estimation unit 16 multiplies the integral value expressed by the Formula (2) by a proportionality constant K. The estimation unit 16 can then calculate the following value, by normalizing the resultant value by dividing it by the total power (the square of I), i.e. a DC component, of the received light signal so as not to depend on the light reception intensity of light such as laser light (Formula (3)):

$$\frac{K \int f \cdot P(f) df}{I^2}. \quad (3)$$

The estimation unit 16 can then estimate the flow state of the fluid A to be measured, by comparing the value of the Formula (3) calculated for the fluid to be measured and the value of the Formula (3) calculated for the fluid in a known flow state measured beforehand (step S5).

Figure 6:
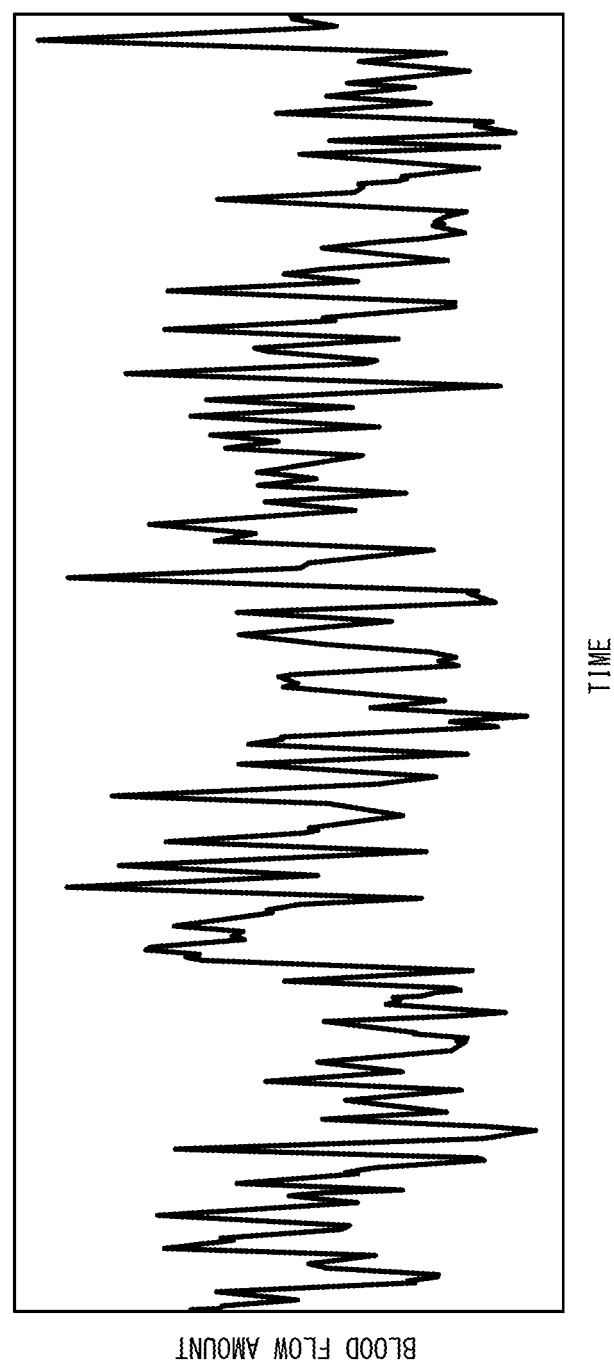
FIG. 6 is a diagram for explaining the principle of fluid measurement according to an embodiment.

FIG. 6 is a diagram illustrating an example of the flow amount of the fluid calculated as described above. For example, the flow amount can be measured from the frequency spectrum P(f) generated from the beat signal at each given time. FIG. 6 is a diagram in which an example of temporal changes in the measured flow amount is plotted. FIG. 6 illustrates temporal changes in the flow amount of the fluid that is blood, i.e. the blood flow amount, as an example. In FIG. 6, the vertical axis represents the flow amount of blood (blood flow amount), and the horizontal axis represents time. The blood flow amount in the vertical axis is in arbitrary units.

The fluid measurement apparatus 1 according to an embodiment can also estimate information such as the flow velocity of the fluid A, based on information such as the cross-sectional area of the flow channel 70.

Thus, the fluid measurement apparatus 1 according to an embodiment can calculate the flow amount of the fluid or the like from the frequency spectrum P(f) generated from the beat signal.

In an embodiment, the fluid measurement apparatus 1 includes the estimation unit 16. The estimation unit 16 can estimate the flow state of the fluid A. In more detail, the estimation unit 16 can estimate the flow state of the fluid A based on the first light Lr1 shifted in frequency. Here, the estimation unit 16 may estimate the flow state of the fluid A based on the difference between the frequency of the first light Lr1 and the frequency of the second light Lr2. The optical detector 64 may receive scattered light that is light emitted from the second optical emitter 62 and scattered by the flow channel 70, and the first light Lr1. The estimation unit 16 may then estimate the flow state of the fluid A, based on the difference between the frequency of the scattered light emitted from the second optical emitter 62 and scattered by the flow channel 70 and the frequency of the first light Lr1.

As described above, with the fluid measurement apparatus 1 according to an embodiment, the flow state (e.g. flow velocity or flow amount) of the fluid can be measured appropriately and accurately under various conditions. Moreover, with the fluid measurement apparatus 1 according to an embodiment, even in the case where the fluid A is a colorless and transparent liquid such as water, the flow state (e.g. flow velocity or flow amount) can be measured appropriately and accurately. The fluid measurement apparatus 1 according to an embodiment therefore offers high convenience.

Conventionally, a flowmeter that uses the principle of Doppler shift calculates the flow amount of a fluid, for example, through arithmetic operations using primary moment for a spectrum obtained as a result of FFT analysis of a Doppler phenomenon caused by an object irradiated with laser light. For example, a laser Doppler flowmetry (LDF) method is conventionally known as a method of measuring blood flow using laser light. The fluid measurement apparatus 1 according to an embodiment can calculate the flow amount of blood or the like by the LDF method using only one optical emitter (second optical emitter 62) and one optical detector (optical detector 64).

However, a transparent liquid such as water does not cause favorable backward scattering of laser light. It is therefore conventionally difficult to favorably estimate the flow state of a fluid such as a transparent liquid in some cases. The following will examine the measurement of the flow amount of a transparent liquid such as water.

Figure 7:
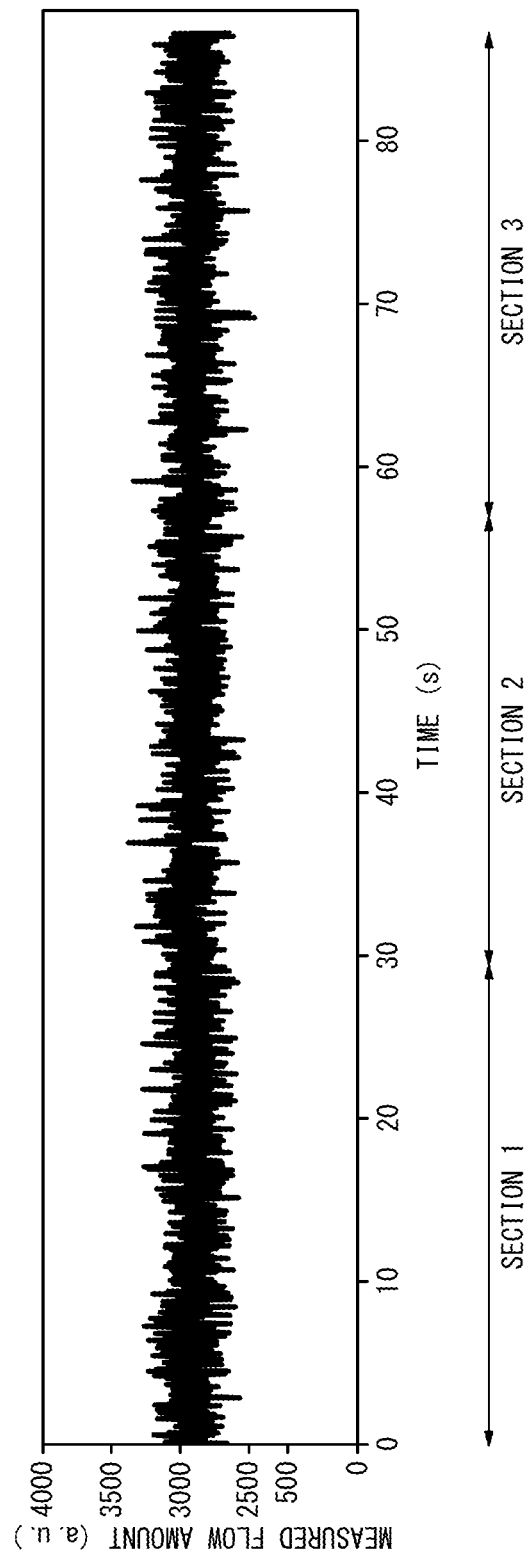
FIG. 7 is a diagram for explaining the principle of fluid measurement according to an embodiment.

FIG. 7 is a diagram illustrating an example of measuring the flow amount of a transparent liquid such as water based on a conventional technique. The measurement illustrated in FIG. 7 can be regarded as an example of calculating the flow amount of the transparent liquid using only the sensor 60 (i.e. without using the first optical emitter 61) in the fluid measurement apparatus 1 according to an embodiment. This result is equally obtained in the case of performing measurement by the conventional LDF method using the same structure.

In the measurement illustrated in FIG. 7, a transparent liquid such as water flows in a flow channel of 2 mm in diameter, as an example. In the measurement illustrated in FIG. 7, the fluid in a flow amount known beforehand is caused to flow using, for example, a pump capable of causing the fluid to flow in a set flow amount. That is, in the example illustrated in FIG. 7, a known flow amount is actually measured to determine measurement accuracy.

In FIG. 7, the horizontal axis represents elapsed time (sec), and the vertical axis represents the flow amount measured (arbitrary units). In the example illustrated in FIG. 7, the flow amount of the fluid is changed among sections 1, 2, and 3. Specifically, in the section 1, the fluid flows in a flow amount of 0 ml/min (i.e. the fluid is (approximately) stationary). In the section 2, the fluid flows in a flow amount of 3 ml/min. In the section 3, the fluid flows in a flow amount of 6 ml/min. However, despite the flow amount of the fluid being actually changed for each section, such change for each section is not observed in the measured flow amount, as illustrated in FIG. 7.

The example illustrated in FIG. 7 can be supposed as an example of measuring the fluid using only the sensor 60 (i.e. without using the first optical emitter 61) in the fluid measurement apparatus 1 illustrated in FIG. 1, as mentioned above. At least part of light emitted from the second optical emitter in the sensor 60 is interfacially reflected by the flow channel 70 and then received by the optical detector 64. Light not interfacially reflected by the flow channel 70 from among the light emitted from the second optical emitter in the sensor 60 toward the flow channel 70 is transmitted through the fluid A. In this case, since the fluid A is transparent, the light is hardly scattered backward by the fluid A flowing in the flow channel 70. In other words, the optical detector 64 can hardly receive backward scattered light by the fluid A from among the light emitted from the second optical emitter. This is considered to be the reason why, despite the flow amount of the fluid being actually changed for each section, such change for each section is not observed in the measured flow amount, as can be seen in the example illustrated in FIG. 7.

In the fluid measurement apparatus 1 according to an embodiment, on the other hand, the optical detector 64 can receive not only light emitted from the second optical emitter 62 but also light emitted from the first optical emitter 61, as illustrated in FIGS. 1 and 2. Here, the optical detector 64 can receive at least part (scattered light Lr2) of light scattered by the flow channel 70 from among light (incident light Le2) emitted from the second optical emitter 62 toward the flow channel 70. The optical detector 64 can also receive at least part (scattered light Lr1) of light transmitted through the fluid A flowing in the flow channel 70 from among light (incident light Le1) emitted from the first optical emitter 61 toward the flow channel 70.

The scattered light Le1 is light (first light Lr1) shifted in frequency as a result of being transmitted through the fluid A flowing in the flow channel 70 from among light emitted from the first optical emitter 61 and received by the optical detector 64, as mentioned above. The scattered light Lr2 is light (second light Lr2) not shifted in frequency from among light emitted from the second optical emitter 62 and received by the optical detector 64, as mentioned above. Hence, in the fluid measurement apparatus 1 according to an embodiment, the estimation unit 16 can estimate the flow state of the fluid A based on the first light Lr1.

In more detail, the estimation unit 16 may estimate the flow state of the fluid A based on the difference between the frequency of the first light Lr1 and the frequency of the second light Lr2. Specifically, the estimation unit 16 may estimate the flow state of the fluid A based on the difference between the frequency of the scattered light scattered by the flow channel 70 from among the light emitted from the second optical emitter 62 and the frequency of the first light Lr1.

Figure 8:
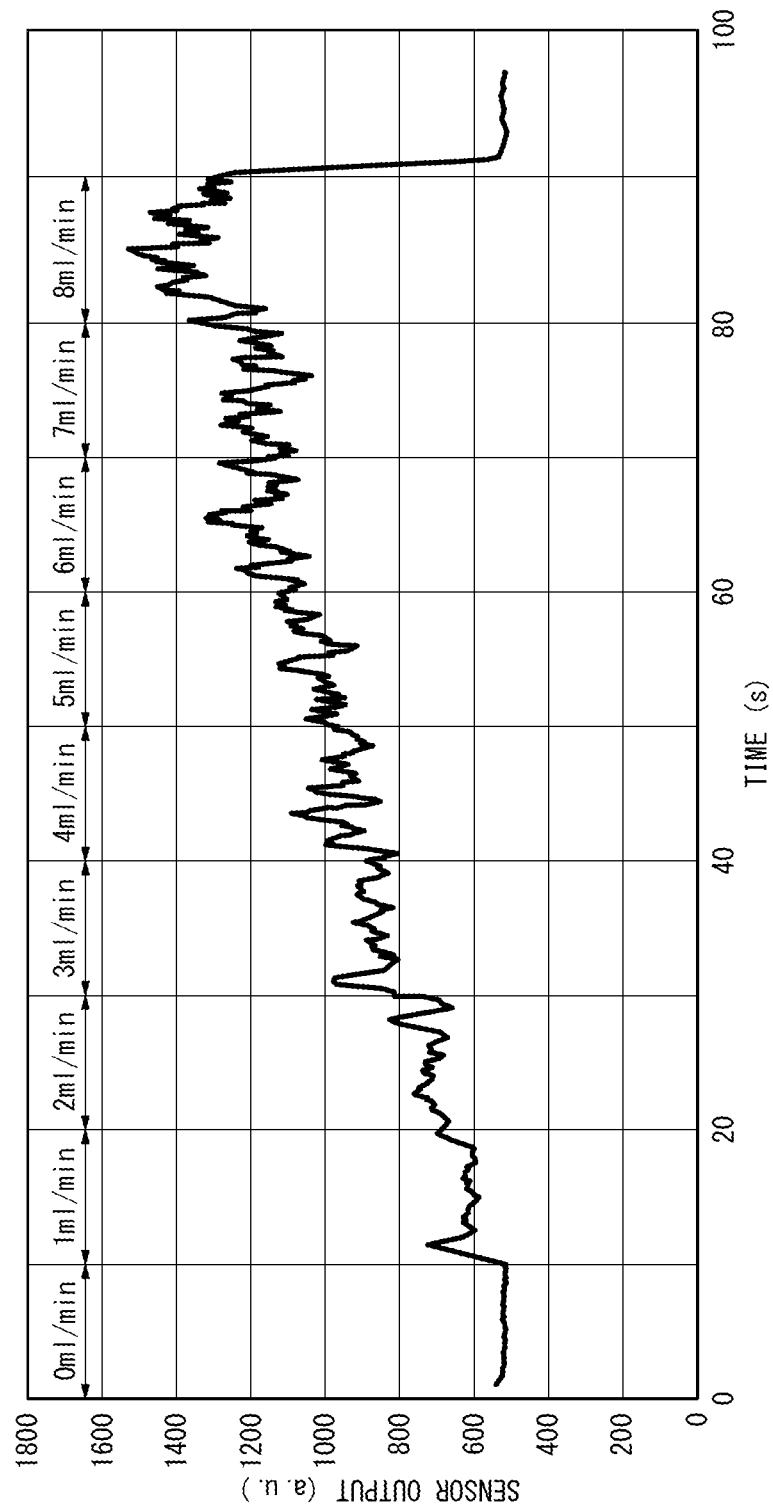
FIG. 8 is a diagram for explaining the principle of fluid measurement according to an embodiment.

FIG. 8 is a diagram illustrating an example of measuring a fluid that is a transparent liquid such as water in the fluid measurement apparatus 1 illustrated in FIGS. 1 and 2. FIG. 8 illustrates an example of measuring a fluid that is a transparent liquid in a state in which not only the sensor 60 but also the first optical emitter 61 is appropriately operated in the fluid measurement apparatus 1 according to an embodiment. In FIG. 8, the horizontal axis represents elapsed time (sec), and the vertical axis represents the flow amount measured (arbitrary units). In the measurement illustrated in FIG. 8, too, the fluid in a flow amount known beforehand is caused to flow using, for example, a pump capable of causing the fluid to flow in a set flow amount. That is, in the example illustrated in FIG. 8, too, a known flow amount is actually measured to determine measurement accuracy.

In FIG. 8, the flow amount in the vertical axis is indicated as sensor output. Herein, the "sensor output" may be, for example, the intensity of light received by the optical detector 64 in the sensor 60 in the fluid measurement apparatus 1 according to an embodiment. As the intensity of light received by the optical detector 64, for example, voltage value may be detected as signal output from the optical detector 64. The signal output is, however, not limited to voltage as long as it indicates temporal changes in the intensity of signal output, and may be current value, resistance value, or the like.

In the example illustrated in FIG. 8, sections of 10 sec are set from the measurement start, and the flow amount of the fluid is changed for each section. Specifically, in the section from the measurement start to 10 sec, the fluid flows in a flow amount of 0 ml/min (i.e. the fluid is (approximately) stationary). In the section from 10 sec to 20 sec, the fluid flows in a flow amount of 1 ml/min. In the section from 20 sec to 30 sec, the fluid flows in a flow amount of 2 ml/min. In the section from 30 sec to 40 sec, the fluid flows in a flow amount of 3 ml/min. The flow amount is equally increased gradually in subsequent sections.

It was confirmed that, in the fluid measurement apparatus 1 according to an embodiment, the sensor output increases with the gradually increased flow amount. Here, the optical detector 64 can receive light reflected by the flow channel 70, as the second light Lr2. The optical detector 64 can also receive light Doppler-shifted as a result of being transmitted through the fluid that is a transparent liquid such as water, as the first light Lr1. The fluid measurement apparatus 1 according to an embodiment can acquire a beat based on interference between the second light Lr2 and the first light Lr1. In other words, the fluid measurement apparatus 1 according to an embodiment can measure even a fluid that is a transparent liquid such as water. As described above, with the fluid measurement apparatus 1 according to an embodiment, even in the case where the fluid A is a transparent liquid such as water, the flow state (e.g. flow velocity or flow amount) can be measured appropriately and accurately. The fluid measurement apparatus 1 according to an embodiment therefore offers high convenience.

In the case of measuring a transparent fluid or the like by the optical detector 64 receiving both light emitted from the first optical emitter 61 and light emitted from the second optical emitter 62 as described above, the balance between the light quantity of light output from the first optical emitter 61 and the light quantity of light output from the second optical emitter 62 is important. Adjustment of the balance between the light quantity of light output from the first optical emitter 61 and the light quantity of light output from the second optical emitter 62 in the fluid measurement apparatus 1 according to an embodiment will be described below.

In the fluid measurement apparatus 1 according to an embodiment, in the case where the output based on the first light Lr1 and the output based on the second light Lr2 from among the signal output of the optical detector 64 based on the received light are not balanced, it may be difficult to favorably detect the beat formed by the first light Lr1 and the second light Lr2. If the beat formed by the first light Lr1 and the second light Lr2 cannot be favorably detected, the fluid measurement apparatus 1 according to an embodiment is likely to have difficulty in measuring the flow amount of a transparent liquid or the like with favorable accuracy. In view of this, in the fluid measurement apparatus 1 according to an embodiment, the balance between the output based on light emitted from the first optical emitter 61 and the output based on light emitted from the second optical emitter 62 from among the signal output of the optical detector 64 may be adjustable. Specifically, the adjustor 18 may be capable of adjusting the light quantity of light received by the optical detector 64. This improves the usefulness of the fluid measurement apparatus 1 because the signal output of the optical detector 64 can be adjusted to enable detection of the difference between the frequency of the first light Lr1 and the frequency of the second light Lr2. Such light quantity adjustment in the fluid measurement apparatus 1 according to an embodiment can be performed in various ways. Some typical examples will be described below.

(1) Adjustment of Light Quantity of Light Emitted from First Optical Emitter 61 and/or the Second Optical Emitter 62

For example, in the fluid measurement apparatus 1 according to an embodiment, the adjustor 18 may adjust the light quantity of light emitted from at least one of the first optical emitter 61 and the second optical emitter 62, through the driver 50. That is, the adjustor 18 can adjust the light quantity of received light by increasing or decreasing the light quantity of light emitted from the first optical emitter 61 and/or the second optical emitter 62.

In this case, the adjustor 18 may adjust the power supplied from the driver 50 to the first optical emitter 61 and/or the second optical emitter 62. The adjustor 18 may adjust the current or voltage supplied from the driver 50 to the first optical emitter 61 and/or the second optical emitter 62. For example, an electrically-operated or manually-operated slit or the like may be provided in the first optical emitter 61 and/or the second optical emitter 62, to enable adjustment of the light quantity of light emitted from the first optical emitter 61 and/or the second optical emitter 62. In this case, the adjustor 18 may adjust the state of the slit or the like provided in the first optical emitter 61 and/or the second optical emitter 62, for example through the driver 50. The adjustor 18 may adjust the light reception sensitivity of the optical detector 64. Instead of the slit or the like, for example, any filter may be provided in the first optical emitter 61 and/or the second optical emitter 62.

(2) Adjustment of Position of at Least One of First Optical Emitter 61, Second Optical Emitter 62, Optical Detector 64, and Flow Channel 70

For example, a displacement mechanism that can be driven by a motor or the like may be provided in at least one of the first optical emitter 61, the second optical emitter 62, the optical detector 64, and the flow channel 70, to enable adjustment of its position. This can change the light quantity of light received by the optical detector 64. The fluid measurement apparatus 1 can thus adjust the light quantity of received light to enable detection of the difference between the frequency of the first light Lr1 and the frequency of the second light Lr2.

Figure 9:
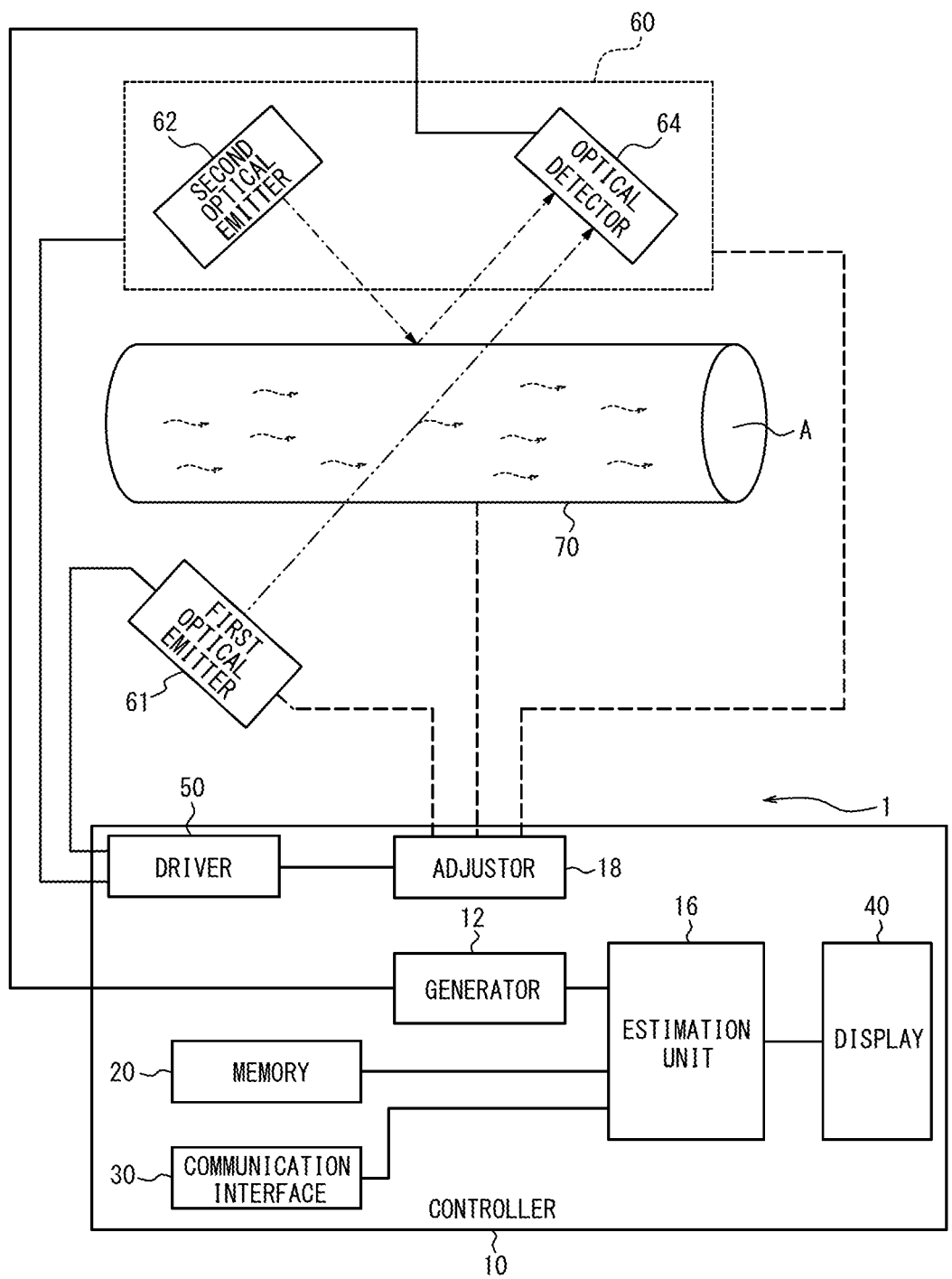
FIG. 9 is a block diagram illustrating an example of a schematic structure of a fluid measurement apparatus according to an embodiment.

FIG. 9 is a diagram illustrating the adjustor 18 capable of adjusting the position of at least one of the first optical emitter 61, the second optical emitter 62, the optical detector 64, and the flow channel 70 in the fluid measurement apparatus 1 according to an embodiment. In FIG. 9, control lines connecting the adjustor 18 to the first optical emitter 61, the sensor 60 (second optical emitter 62 and optical detector 64), and the flow channel 70 are indicated by dashed lines. Suppose a displacement mechanism that can be driven by a motor or the like is provided in at least one of the first optical emitter 61, the second optical emitter 62, the optical detector 64, and the flow channel 70 connected to the adjustor 18 by a control line in FIG. 9.

The adjustor 18 is connected to at least one of the first optical emitter 61, the second optical emitter 62, the optical detector 64, and the flow channel 70 by a control line, to drive the displacement mechanism provided in the at least one of the first optical emitter 61, the second optical emitter 62, the optical detector 64, and the flow channel 70. With such a structure, the adjustor 18 may adjust the position of at least one of the first optical emitter 61, the second optical emitter 62, the optical detector 64, and the flow channel 70 in the fluid measurement apparatus 1 according to an embodiment. Specifically, for example, the adjustor 18 may adjust the distance between the optical detector 64 and the first optical emitter 61 and/or the second optical emitter 62, to adjust the light quantity of light emitted from the first optical emitter 61 and/or the second optical emitter 62 and received by the optical detector 64. The adjustor 18 may adjust the position of at least one of the first optical emitter 61, the second optical emitter 62, and the optical detector 64 relative to the flow channel 70.

The displacement mechanism is not limited to an electrically-operated mechanism. For example, at least one of the first optical emitter 61, the second optical emitter 62, the optical detector 64, and the flow channel 70 may be provided with a displacement mechanism capable of manually changing position. In this case, the user can adjust the light quantity of received light by, for example, adjusting the position while checking the measurement result displayed on the display device. This improves the usefulness of the fluid measurement apparatus 1 while reducing power consumption.

(3) Adjustment of Orientation (Angle) of at Least One of First Optical Emitter 61, Second Optical Emitter 62, Optical Detector 64, and Flow Channel 70

For example, a rotation mechanism that can be driven by a motor or the like may be provided in at least one of the first optical emitter 61, the second optical emitter 62, the optical detector 64, and the flow channel 70, to enable adjustment of its orientation (angle). This can change the light quantity of received light. The fluid measurement apparatus 1 can thus adjust the light quantity of received light to enable detection of the difference between the frequency of the first light Lr1 and the frequency of the second light Lr2. The rotation mechanism is any mechanism that realizes at least part of rotation motion. In detail, the rotation mechanism need not necessarily realize rotation motion of one turn, and may realize, for example, rotation motion of a half turn or a ¼ turn. Rotation is not limited to one direction. That is, the rotation mechanism may realize rotation motion of 360 degrees.

FIG. 9 is a diagram illustrating the adjustor 18 capable of adjusting the orientation (angle) of at least one of the first optical emitter 61, the second optical emitter 62, the optical detector 64, and the flow channel 70 in the fluid measurement apparatus 1 according to an embodiment. In FIG. 9, control lines connecting the adjustor 18 to the first optical emitter 61, the sensor 60 (second optical emitter 62 and optical detector 64), and the flow channel 70 are indicated by dashed lines. Suppose a rotation mechanism that can be driven by a motor or the like is provided in at least one of the first optical emitter 61, the second optical emitter 62, the optical detector 64, and the flow channel 70 connected to the adjustor 18 by a control line in FIG. 9.

The adjustor 18 is connected to at least one of the first optical emitter 61, the second optical emitter 62, the optical detector 64, and the flow channel 70 by a control line, to drive the rotation mechanism provided in the at least one of the first optical emitter 61, the second optical emitter 62, the optical detector 64, and the flow channel 70. With such a structure, the adjustor 18 may adjust the orientation (angle) of at least one of the first optical emitter 61, the second optical emitter 62, the optical detector 64, and the flow channel 70 in the fluid measurement apparatus 1 according to an embodiment.

Specifically, for example by changing the orientation (angle) of the optical detector 64, the adjustor 18 can change the solid angle of light incident from one direction. For example, in the case where, when the optical detector 64 receives light emitted from one direction, the light receiving surface of the optical detector 64 is perpendicular to the travelling direction of light, the solid angle of light received by the light receiving surface of the optical detector 64 is at its maximum. In this case, the quantity of light received by the light receiving surface of the optical detector 64 is expected to be near maximum. On the other hand, in the case where, when the optical detector 64 receives light emitted from one direction, the light receiving surface of the optical detector 64 is not perpendicular to the travelling direction of light, the solid angle of light received by the light receiving surface of the optical detector 64 is smaller. In other words, the solid angle of light received by the light receiving surface of the optical detector 64 is smaller if light is incident on the light receiving surface of the optical detector 64 from an oblique direction. In this case, the solid angle of light received by the light receiving surface of the optical detector 64 can be decreased with an increase of the incidence angle of light on the light receiving surface of optical detector 64. Consequently, the light quantity of received light can be decreased.

Thus, in an embodiment, the adjustor 18 may adjust the incidence angle (incidence angle 1) of light emitted from the first optical emitter 61 and received by the optical detector 64 with respect to the optical detector 64. Moreover, in an embodiment, the adjustor 18 may adjust the incidence angle (incidence angle 2) of light emitted from the second optical emitter 62 and received by the optical detector 64 with respect to the optical detector 64. The adjustor 18 may adjust at least one of the incidence angle 1 and the incidence angle 2.

The rotation mechanism is not limited to an electrically-operated mechanism. For example, at least one of the first optical emitter 61, the second optical emitter 62, the optical detector 64, and the flow channel 70 may be provided with a rotation mechanism capable of manually changing orientation (angle).

Thus, in an embodiment, the adjustor 18 may adjust the light quantity of light emitted from at least one of the first optical emitter 61 and the second optical emitter 62 and received by the optical detector 64, to enable detection of the difference between the frequency of the first light Lr1 and the frequency of the second light Lr2.

Measurement in the fluid measurement apparatus 1 according to an embodiment in the case where the fluid A that is a transparent liquid such as water flows in the flow channel 70 will be described below.

In the fluid measurement apparatus 1 according to an embodiment, the optical detector 64 may be unable to favorably detect the flow state of the fluid A when the fluid A flows in the flow channel 70. For example, in the case where the direction in which the fluid A flows in the flow channel 70 and the direction in which the first optical emitter 61 emits light are orthogonal to each other, the Doppler shift when the light emitted from the first optical emitter 61 is transmitted through the fluid A is likely to be small. In such a case, there is a possibility that the Doppler shift cannot be detected with sufficient sensitivity, depending on the structures of the first optical emitter 61 and the optical detector 64.

In view of this, the fluid measurement apparatus 1 according to an embodiment may have an arrangement wherein the direction in which the fluid A flows in the flow channel 70 and the direction in which the first optical emitter 61 emits light are not orthogonal to each other. For example, in FIGS. 1 and 2, light emitted from the first optical emitter 61 is transmitted through the fluid A at an angle of approximately 45 degrees with respect to the flow channel 70. That is, in an embodiment, the first optical emitter 61 may emit light having a component in a direction parallel to the flow direction of the fluid A. Herein, the "direction parallel to the flow direction of the fluid A" with regard to the light emitted from the first optical emitter 61 is not limited to the same direction as the direction in which the fluid A flows, and may be the opposite direction from the direction in which the fluid A flows.

With such an arrangement, the Doppler shift when light emitted from the first optical emitter 61 is transmitted through the fluid A can be increased. This improves measurement sensitivity in the fluid measurement apparatus 1 according to an embodiment. The usefulness of the fluid measurement apparatus 1 can thus be improved.

When changing the direction of light emitted from the first optical emitter 61 with respect to the flow channel 70, the first optical emitter 61 and/or the flow channel 70 may be provided with an appropriate displacement mechanism and/or a rotation mechanism, as mentioned above. The displacement mechanism and/or the rotation mechanism may be automatically operated or manually operated.

In this case, too, the signal output of the optical detector 64 may be adjusted using, for example, the displacement mechanism and/or the rotation mechanism provided in the optical detector 64 and/or the flow channel 70. For example, in the case where the direction of the first optical emitter 61 is changed, at least one of the light emission intensity, position, and orientation (angle) of the first optical emitter 61 may be adjusted depending on the changed direction of the first optical emitter 61. For example, in the case where the direction of the first optical emitter 61 is changed, at least one of the light reception sensitivity, position, and orientation (angle) of the optical detector 64 may be adjusted depending on the changed direction of the first optical emitter 61.

Thus, in an embodiment, the adjustor 18 may adjust at least one of the incidence angle of light emitted from the first optical emitter 61 with respect to the flow channel 70 and the incidence angle of light emitted from the second optical emitter 62 with respect to the flow channel 70.

While some embodiments of the present disclosure have been described above by way of drawings and examples, various changes or modifications may be easily made by those of ordinary skill in the art based on the present disclosure. Such various changes or modifications are therefore included in the scope of the present disclosure. For example, the functions included in the functional units, etc. may be rearranged without logical inconsistency, and a plurality of functional units, etc. may be combined into one functional unit, etc. and a functional unit, etc. may be divided into a plurality of functional units, etc. Moreover, each of the disclosed embodiments is not limited to the strict implementation of the embodiment, and features may be combined or partially omitted as appropriate.

For example, although the sensor 60 includes the second optical emitter 62 and the optical detector 64 and the first optical emitter 61 is provided separately in the example illustrated in FIGS. 1 and 9, the structure of the first optical emitter 61, the second optical emitter 62, and the optical detector 64 is not limited to the example illustrated in FIGS. 1 and 9, and may be any of various structures. For example, the first optical emitter 61, the second optical emitter 62, and the optical detector 64 may each be provided separately. Alternatively, the first optical emitter 61, the second optical emitter 62, and the optical detector 64 may all be included in a sensor in one package. Moreover, a reflector may be installed in at least part of the flow channel or outside the flow channel so as to reflect transmitted light. Such a fluid measurement apparatus 1 can receive reflected light of transmitted light and measure the flow amount. In this case, the optical path length of received light increases, with it being possible to achieve more suitable measurement. The fluid measurement apparatus 1 need not necessarily include two different optical emitters, i.e. the first optical emitter 61 and the second optical emitter 62. In other words, a simpler sensor structure may be used.

Figure 10:
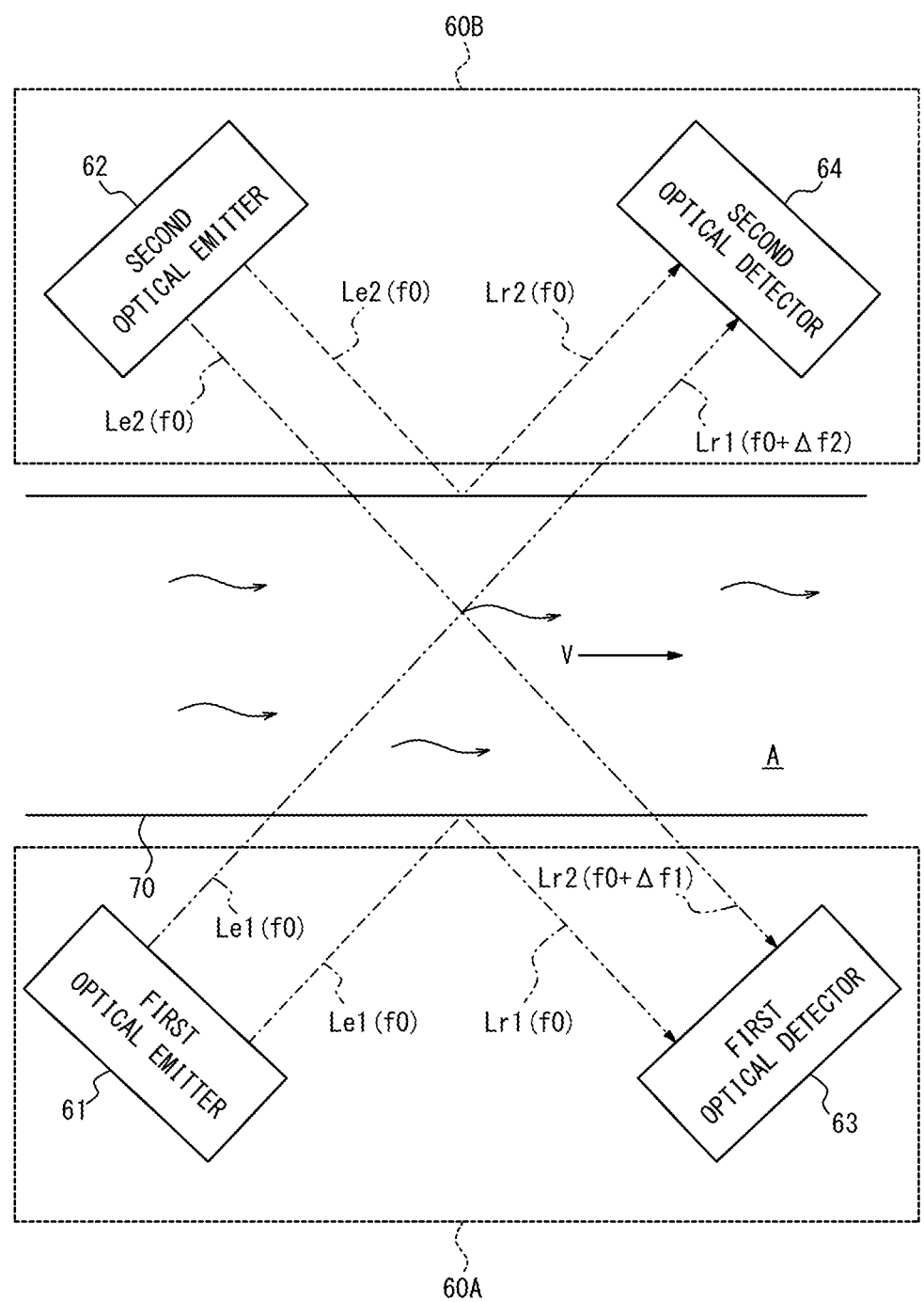
FIG. 10 is a diagram for explaining detection of scattered light in fluid measurement according to an embodiment.

For example, two sensors in each of which an optical emitter and an optical detector are included in one package may be used to ease measurement by the fluid measurement apparatus 1 according to an embodiment, as illustrated in FIG. 10.

In the example illustrated in FIG. 10, a first sensor 60A includes the first optical emitter 61 and a first optical detector 63, and a second sensor 60B includes the second optical emitter 62 and second optical detector 64. In such a structure, for example, the first optical detector 63 in the first sensor 60A receives at least part of light emitted from the first optical emitter 61 and scattered by the flow channel 70. The first optical detector 63 also receives at least part of light emitted from the second optical emitter 62 and transmitted through the fluid A flowing in the flow channel 70. Thus, even in the case where the fluid A is a transparent liquid such as water, the flow state can be measured appropriately and accurately. A highly convenient fluid measurement apparatus can therefore be provided. Moreover, simply by preparing two sensors each of which includes an optical emitter and an optical detector and arranging them to face each other in a staggered configuration, the sensors in the fluid measurement apparatus 1 according to an embodiment can be configured easily.

The foregoing embodiments are not limited to embodiments as the fluid measurement apparatus 1. For example, the foregoing embodiments may be carried out as a fluid measurement method performed in the fluid measurement apparatus 1 or a program executed by a computer that controls an apparatus such as the fluid measurement apparatus 1.

A fluid measurement method according to an embodiment comprises: emitting light to an irradiated object that includes a fluid; receiving first received light transmitted through the fluid to thereby be shifted in frequency; and estimating a flow state of the fluid based on the first received light.

A program according to an embodiment causes a computer to execute: emitting light from a first optical emitter to an irradiated object that includes a fluid; receiving, by an optical detector, first received light emitted from the first optical emitter and transmitted through the fluid to thereby be shifted in frequency; and estimating, by an estimation unit, a flow state of the fluid based on the first received light.

REFERENCE SIGNS LIST 1 fluid measurement apparatus
10 controller
12 generator
16 estimation unit 18 adjustor
20 memory
30 communication interface
40 display
50 driver
60 sensor
61 first optical emitter
62 second optical emitter
64 optical detector
70 flow channel

The invention claimed is:

1. A fluid measurement apparatus comprising:
 a first optical emitter configured to emit light to an irradiated object that includes a transparent fluid;
 a second optical emitter configured to emit light to the irradiated object,
 an optical detector configured to receive first received light emitted from the first optical emitter and transmitted through the transparent fluid, the optical detector further configured to receive second received light emitted from the second optical emitter, wherein the first received light is Doppler-shifted in frequency and the second received light is not shifted in frequency; and
 an estimation unit configured to estimate a flow state of the transparent fluid based on a difference between a frequency of the first received light and a frequency of the second received light.

2. The fluid measurement apparatus according to claim 1, wherein the irradiated object includes a flow channel in which the transparent fluid flows, and
 the second optical emitter is located on an opposite side of the flow channel from the first optical emitter, in a planar view in a direction in which the transparent fluid flows in the flow channel.

3. The fluid measurement apparatus according to claim 2, wherein the optical detector is configured to receive the first received light and scattered light that is emitted from the second optical emitter and scattered by the flow channel, and
 the estimation unit is configured to estimate the flow state of the transparent fluid based on a difference between the frequency of the first received light and a frequency of the scattered light.

4. The fluid measurement apparatus according to claim 1, further comprising
 an adjustor configured to adjust a light quantity of light received by the optical detector,
 wherein the adjustor is configured to adjust at least one of: a light quantity of light emitted from the first optical emitter and received by the optical detector; and a light quantity of light emitted from the second optical emitter and received by the optical detector.

5. The fluid measurement apparatus according to claim 4, wherein the adjustor is configured to adjust at least one of: a light quantity of the light emitted from the first optical emitter; and a light quantity of the light emitted from the second optical emitter.

6. The fluid measurement apparatus according to claim 4, wherein the adjustor is configured to adjust a position of at least one of the first optical emitter, the second optical emitter, the optical detector, and the flow channel.

7. The fluid measurement apparatus according to claim 4, wherein the adjustor is configured to adjust at least one of: an incidence angle of the light emitted from the first optical emitter and received by the optical detector, with respect to the optical detector; and an incidence angle of the light emitted from the second optical emitter and received by the optical detector, with respect to the optical detector.

8. The fluid measurement apparatus according to claim 4, wherein the adjustor is configured to adjust at least one of: an incidence angle of the light emitted from the first optical emitter, with respect to the flow channel; and an incidence angle of the light emitted from the second optical emitter, with respect to the flow channel.

9. The fluid measurement apparatus according to claim 1, wherein the first optical emitter is configured to emit light that has a component in a direction parallel to a flow direction of the transparent fluid.

10. The fluid measurement apparatus according to claim 1, wherein at least part of the transparent fluid has translucency.

11. A fluid measurement method comprising:
 emitting light from a first optical emitter to an irradiated object that includes a transparent fluid;
 emitting light from a second optical emitter to the irradiated object;
 receiving at an optical detector first received light transmitted through the transparent fluid, wherein the first received light is Doppler-shifted in frequency;
 receiving at the optical detector second received light, wherein the second received light is not shifted in frequency; and
 estimating a flow state of the transparent fluid based on a difference between a frequency of the first received light and a frequency of the second received light.

12. The fluid measurement method according to claim 11, wherein the irradiated object further includes a flow channel in which the transparent fluid flows,
 the second received light is scattered light that is light scattered by the flow channel, and
 the flow state of the transparent fluid is estimated based on a difference between the frequency of the first received light and a frequency of the scattered light.

13. The fluid measurement method according to claim 11, further comprising
 adjusting at least one of an intensity of emitted light and an intensity of received light.

14. A non-transitory computer-readable recording medium that stores a control program, the control program configured to control a measurement apparatus to execute process of:
 emitting light from a first optical emitter to an irradiated object that includes a transparent fluid;
 emitting light from a second optical emitter to the irradiated object;
 receiving, by an optical detector, first received light emitted from the first optical emitter and transmitted through the transparent fluid, wherein the first received light is Doppler-shifted in frequency;
 receiving, by the optical detector, second received light emitted from the second optical emitter, wherein the second received light is not shifted in frequency; and
 estimating, by an estimation unit, a flow state of the transparent fluid based on a difference between a frequency of the first received light and a frequency of the second received light.

* * * * *